United States Patent [19]
Schneider et al.

[11] Patent Number: 5,217,937
[45] Date of Patent: Jun. 8, 1993

[54] SIO$_2$-CONTAINING COOPER OXIDE-CHROMIUM OXIDE CATALYST FOR THE HYDROGENATION OF FATTY ACIDS AND FATTY ESTERS

[75] Inventors: Michael Schneider, Ottobrunn-Riemerling; Gerd Maletz, Brückmühl; Karl Kochloefl, Brückmühl/Heufeld, all of Fed. Rep. of Germany

[73] Assignee: Süd-Chemie Aktiengesellschaft, Munich, Fed. Rep. of Germany

[21] Appl. No.: 795,493

[22] Filed: Nov. 21, 1991

[30] Foreign Application Priority Data

Nov. 27, 1990 [DE] Fed. Rep. of Germany ....... 4037729

[51] Int. Cl.$^5$ .............. B01J 21/06; B01J 21/08; B01J 23/10; B01J 23/26; B01J 23/72
[52] U.S. Cl. ................... 502/242; 502/244; 502/524; 568/885
[58] Field of Search ........... 502/242, 244, 524; 568/885

[56] References Cited

U.S. PATENT DOCUMENTS

| | | | |
|---|---|---|---|
| 3,756,964 | 9/1973 | Frazee et al. | 252/454 |
| 3,767,595 | 10/1973 | Montgomery | 252/454 |
| 4,666,879 | 5/1987 | Kelly et al. | 502/318 X |
| 4,855,273 | 8/1989 | Pohl | 502/244 |
| 4,935,556 | 6/1990 | Pohl | 568/885 |

FOREIGN PATENT DOCUMENTS

| | | | |
|---|---|---|---|
| 300346 | 1/1989 | European Pat. Off. | 568/885 |
| 3823458 | 4/1990 | Fed. Rep. of Germany . | |

*Primary Examiner*—W. J. Shine
*Attorney, Agent, or Firm*—Herbert P. Price

[57] ABSTRACT

An SiO$_2$-containing copper oxide-chromium oxide catalyst is obtained through heat treatment of copper oxide and chromium oxide, or of a precursor compound convertible into copper oxide or chromium oxide in the presence of an SiO$_2$ component; it is characterized by the fact that, after the heat treatment, (a) the intensity ratio between the X-ray diffraction lines (XRD reflexes) of the copper oxide with d=0.232 nm and of the CuCr$_2$O$_4$ spinel with d=0.240 nm formed through heat treatment, determined as the ratio of the reflex amplitudes, is 0.7 to 4.0:1, and (b) the copper mass, which is dissolved by stirring 10 g of the catalyst in 100 ml of 10 weight percent acetic acid at 20° C. for 2 minutes, amounts to a maximum of 200 mg.

8 Claims, 1 Drawing Sheet

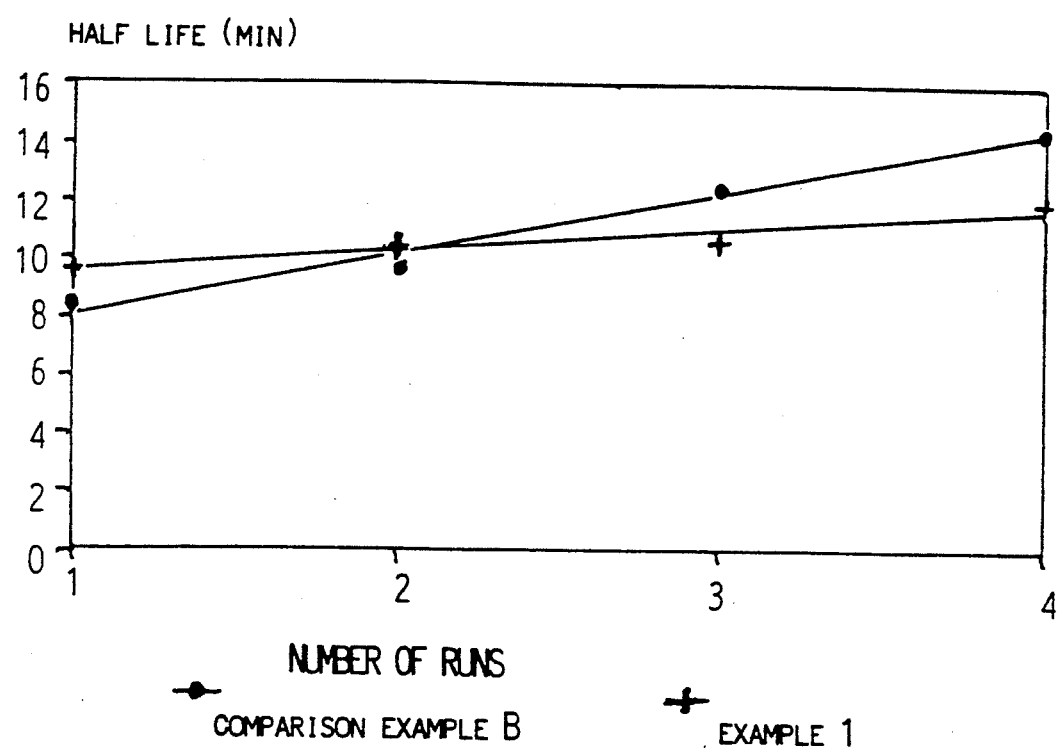

SIO₂-CONTAINING COOPER OXIDE-CHROMIUM OXIDE CATALYST FOR THE HYDROGENATION OF FATTY ACIDS AND FATTY ESTERS

BACKGROUND OF THE INVENTION

The field of art to which this invention is directed is hydrogenation catalysts.

Fatty alcohols, i.e, aliphatic, predominantly linear primary alcohols with chain lengths greater than eight carbon atoms represent especially significant intermediate products in the chemical industry. One of their primary uses is in the production of surfactants such as fatty alkyl sulfates, polyglycol ethers or polyglycol ether sulfates.

The most important raw materials for their production are fatty acids, or fatty acid esters, in the form of mixtures of various chain lengths, which can be obtained, for instance, from natural fats and oils. Conversion into fatty alcohols occurs through catalytic hydrogenation under pressure, for which catalysts based on copper-chromium have proven to be particularly effective.

The hydrogenation reaction is conducted as suspension hydrogenation, as vapor-phase hydrogenation, or in the trickle phase. Sufficiently high reaction rates are only achieved at pressures above 250 bar and temperatures in the 260° to 300° C. range. As a rule, the triglycerides are transesterified with methanol according to known methods before hydrogenation, the free fatty acids being esterified. Nevertheless, the reaction mixture contains a residual concentration of free carboxylic acids.

An important technical embodiment is represented by the suspension hydrogenation of fatty acids according to the LURGI process. In this process the fatty acid mixture is continuously fed to the hydrogenation reactor and esterified in situ by the excess fatty alcohol present.

The presence of the free fatty acids obviously makes great demands on the acid resistance of the catalysts that are used. The catalyst metals—copper, in particular—can be eluted due to the attack of the acids, so that the catalyst's efficacy is impaired. Moreover, this also leads to contamination of the product.

A possible means of reducing the acid solubility of copper-chromium catalysts, is extraction with acetic acid. However, not only is this process particularly expensive, but the hydrogenation activity of the resulting catalyst is significantly reduced, which is not surprising, given the loss of active copper metal through the treatment with acetic acid.

It is further known that the crystallinity of copper-chromium catalysts can be increased through calcination at comparatively high temperatures, whereas the phases present are completely or partially converted into $CuCr_2O_4$ that has a spinel structure depending on the copper-chromium molar ratio. As a result of this heat treatment, on the one hand the solubility in acid of the catalyst metals decreases, but on the other hand the inner surface of the catalyst, as determined by the BET method, is reduced. At the same time a drastic reduction in hydrogenation activity is observed.

German Patent Application No. DE-A-3706658 (EP-A-0 280 982) further indicates a process for the production of a copper (II) chromite catalyst, conceived, however solely for the direct fixed-bed hydrogenation of fatty acids. This process provides for the production of the catalyst in a relatively well-known way using colloidal silica gel, followed by calcination at a temperature of at least 750° C. for a duration of at least 12 hours. Catalysts produced in accordance with this system actually exhibit a high resistance to attack by fatty acids. However, if they are used in the esterification-hydrogenation of fatty acids in the liquid phase (LURGI process), hydrogenation activities are found that are far below the values achieved with commercial copper-chromium catalysts.

From German Patent Application No. DE-A-38 23 458, a process for the dehydrogenation of 1,2-diols with at least three carbon atoms into 1,2-keto alcohols in the presence of copper chromite catalysts is known. Copper oxide catalysts on a supporting material of silicon dioxide or zinc oxide can further be used. The copper chromite catalysts do not contain any more excess copper oxide, while the copper oxide-silicon oxide catalysts are not acid-resistant.

From U.S. Pat. No. 3,756,964 (German Patent Application No. DE-A-23 11 114), supported copper chromite catalysts for hydrogenation reactions are known, where aluminum oxides, silicon oxides, aluminosilicates or mixtures of two or more of these compounds can be used. The active components are located in the pores of the supporting material. Since the calcination temperatures are low, the catalysts obtained still have a relatively high acid solubility.

Finally, U.S. Pat. No. 3,767,595 (German Patent Application No. DE-OS-22 46 382) relates to a process for the production of copper chromite catalysts that can be used for the hydrogenation of esters or aldehydes into alcohols. The catalysts are produced by dissolving metallic copper in an ammonium carbonate solution in the presence of oxygen, reacting the tetraammine copper complex obtained with chromic acid solution or a solution of copper dichromate and calcining the resulting basic copper ammonium chromate for formation of a copper chromite catalyst at approximately 250° to 450° C. The catalysts obtained still have a relatively high acid solubility.

The objective of the present invention is to produce catalysts that combine significantly improved acid resistance with high hydrogenation activity.

SUMMARY OF INVENTION

This invention is directed to copper oxide-chromium oxide hydrogenation catalysts. In one aspect this invention relates to copper oxide-chromium oxide catalysts which are acid resistant and have a high degree of hydrogenation activity. In another aspect, this invention pertains to a process for hydrogenating fatty acids or fatty acid esters or mixtures thereof using copper oxide-chromium oxide catalysts.

The acid resistant catalysts of this invention contain (in analytical terms) about 20 to about 70 weight percent CuO, about 20 to about 70 weight percent $Cr_2O_3$, about 1 to about 25 weight percent $SiO_2$ and 0 to about 15 weight percent of an additional metal oxide component which is a metal oxide selected from aluminum oxide, zirconium oxide, cerium oxide or lanthanum oxide or mixtures thereof. The catalysts after thermal treatment of the metal oxides or precursor compounds convertible into oxides (usually at a temperature of about 300° C. to about 900° C.) have a surface area determined by the BET method, of at least about 8

$m^2/g$. The intensity ratio between X-ray diffraction lines (XRD reflexes) of the copper oxide (d=0.232 nm) and of the $CuCr_2O_4$ spinel formed through heat treatment (d=0.240 nm) determined as the ratio of reflex amplitudes, is about 0.7 to about 4.0:1, preferably, 0.7 to 2.0:1. The acid resistance of the catalyst as determined by measuring the amount of copper dissolved from the catalyst by stirring 10 grams of the catalyst in 10 percent acetic acid at 20° C. for 2 minutes is a maximum of 200 mg. The catalyst of this invention preferably contains (in analytical terms) about 30 to about 55 weight percent CuO, about 30 to about 55 weight percent $Cr_2O_3$, about 2 to about 15 weight percent $SiO_2$ and about 0.5 to about 10 weight percent aluminum oxide, zirconium oxide, cerium oxide or lanthanum oxide or mixtures thereof. Most preferably, the catalyst contains zirconium oxide or cerium oxide.

BRIEF DESCRIPTION OF THE DRAWING

The drawing graphically illustrates the longer half-life activity of the catalyst of the invention.

DESCRIPTION OF INVENTION

The catalysts of this invention are prepared according to methods well-known to those skilled in the art. For instance, solutions of copper nitrate and ammonium chromate, wherein the $SiO_2$ component is added to either the nitrate solution or the ammonium chromate solution, can be precipitated as a copper ammonium chromate complex. The additional metal oxide or precursor compound, if used, can then be added. Precursor compounds which can be converted to oxides are, for example, nitrates, sulfates or carbonates. The precipitated compounds are recovered by filtration and are heat treated.

Pyrogenic or precipitated silicic acid, kieselguhr, silica sol and other colloidal forms, aluminosilicate and/or magnesium silicate are preferably used as the $SiO_2$ component. Pyrogenic silicic acid is particularly advantageous since it is non porous.

Heat treatment is necessary in order to convert the copper-chromium-containing precipitation products into the form according to the invention. This calcination is conducted at temperatures between about 300° and about 900° C., preferably at temperatures between about 500° and about 700° C. The calcination can be conducted statically, e.g. in suitable tray furnaces, as well as continuously, e.g., in rotary kilns. The necessary residence time is to be determined experimentally for the particular calcination unit used. The inner surface of the calcinated product, which is to be determined according to the BET method, is the criterion for this. It should be between about 8 $m^2/g$ and about 60 $m^2/g$, preferably between about 10 $m^2/g$ and about 40 $m^2/g$.

Heat treatment, even for the catalysts according to the invention, does cause a reduction in the BET surface. But surprisingly, it was found that the hydrogenation activity remains nearly unchanged while the acid resistance is significantly increased.

The $SiO_2$ component preferably has a porosity (measured by the nitrogen adsorption method) of <0.1 $cm^3/g$, in particular of <0.05 $cm^3/g$. A non-porous $SiO_2$ component is used to particular advantage.

The nitrogen adsorption method is a standard process for the determination of porosity. In this method, the adsorption and deadsorption isotherms at 77 K (pore volume: capillary condensation at $P_{rel} = 0.99$) are determined using the "Sorptomatic 1800" device manufactured by the Carlo Erba company (see S. J. Gregg and K. S. W. Sing, "Adsorption, Surface Area and Porosity", Academic Press, 1982, p. 116-121). The pore volume is measured for the particles of the $SiO_2$ component and does not take account of the volume between the particles.

Additional promoters can also be introduced, such as those known for the production of copper-chromium catalysts, e.g., compounds of alkaline earth metals or of manganese.

If a metal component containing aluminum, zirconium, cerium and/or lanthanum oxide is introduced, a synergistic effect surprisingly occurs.

The catalysts of this invention are used for the liquid-phase hydrogenation of fatty acids or fatty acid mixtures with 5 to 24 carbon atoms and/or the esters thereof, and in certain cases in admixture with alcohols, into the corresponding fatty alcohols.

The fatty acids or fatty acid mixtures are preferably esterified in situ by the alcohol present in the reaction mixture. Preferably the alcohols present in the reaction mixture will represent fatty alcohols or mixtures of fatty alcohols with 4 to 24 carbon atoms.

The following examples explain the production of copper-chromium catalysts according to the invention and their use for the suspension hydrogenation of fatty acids.

EXAMPLE 1

800 g of chromic acid are dissolved in 2000 ml of deionized water, 1660 g of 25 percent ammonia are added and 136 g of pyrogenic silicic acid with a smooth non-porous surface (CABOSIL LM 150) are dispersed in the ammonium chromate solution that is produced. The dispersion is diluted to a total volume of 8 liters. Copper nitrate containing 447 g of copper is dissolved to a total volume of 500 ml. Precipitation is carried out through admixture of the nitrate solution to the $SiO_2$-containing ammonium chromate solution at 60° C. The filter cake is filtered and calcinated as follows: it is heated to a temperature of 320° C. at a heating rate of 2°/min and maintained at this temperature for one hour; the temperature is then increased to 600° C. at 2°/min and this temperature is then maintained for 3 hours.

The catalyst obtained in this way contains 10 percent $SiO_2$; the BET surface is 18 $m^2/g$. The intensity ratio (I) of the XRD reflexes at d=0.232 nm (CuO) and d=0.240 nm ($CuCr_2O_4$) is 1.3 (I=reflex amplitude at d=0.232 nm/reflex amplitude at d=0.240 nm).

Comparative Example A

A catalyst like that described in Example 1 is produced. Instead of the pyrogenic silicic acid, however, 146 g of colloidal silicic acid (LUDOX AS 40) are added to the nitrate solution and calcination is conducted at 750° C. for 15 hours. (In accord with the system used in DE-A-37 06 658). The BET surface of the resulting catalyst is 14 $m^2/g$, the intensity ratio (I) is found to be 0.3.

Comparative Example B

Precipitation is conducted as described in Example 1. However, no $SiO_2$ component is added to the ammonium chromate solution. The $SiO_2$ - free intermediate stage obtained in this way is calcinated as follows: heating to 320° C. at 2°/min, maintenance at this temperature for one hour, increase of temperature to 370° C.

and maintenance at this temperature for 3 hours. The BET surface is 30 m²/g, the intensity ratio I is 1.1.

Comparative Example C

Production of the catalyst occurs as in Comparative Example B. However, the SiO₂-free intermediate stage obtained is calcinated in analogous fashion to that used in Example 1, i.e., it is heated to a temperature of 320° C. at a heating rate of 2°/min and maintained at this temperature for one hour; the temperature is then increased to 600° C. at 2°/min and this temperature is then maintained for 3 hours. The BET surface as determined at 4 m²/g, the intensity ration I is 0.5.

Example 2 to 6

Using the same procedure described in Example 1, additional copper oxide-chromium oxide catalysts are produced, but with replacement of the pyrogenic silicic acid used there with the SiO₂ components listed below, which are added to the ammonium chromate solution in finely ground form (136 g each). If the pH falls below 6.2 during precipitation, concentrated ammonia is added; the final pH is 6.8. The BET surfaces of the catalysts according to the invention that are obtained are also listed for the purpose of comparison, as are the intensity ratios of the XRD reflexes of CuO at d=0.232 nm and CuCr₂O₄ at d=0.240 nm.

| Example | SiO₂ component | BET surface | I |
|---|---|---|---|
| 2 | kieselguhr | 13 m²/g | 1.1 |
| 3 | precipitated silicic acid | 27 m²/g | 1.1 |
| 4 | silica sol | 14 m²/g | 0.9 |
| 5 | Mg silicate | 16 m²/g | 1.1 |
| 6 | amorphous aluminosilicate | 36 m²/g | 1.1 |

EXAMPLE 7

Catalyst production proceeds as in Example 1, but 69 g of pyrogenic silicic acid (CABOSIL LM 50) is added to the ammonium chromate solution. In addition, the copper nitrate solution is mixed with 339 g of zirconium nitrate solution (20 percent ZrO₂ concentration, GOLDMANN). The catalyst contains 5 percent each of SiO₂ and ZrO₂. Its BET surface amounts to 35 m²/g after calcination at 600° C., the I value is 1.5.

The following test serves to determine the relative resistance to acid attack: 10 g of the catalyst are stirred for 2 min at 20° C. in 100 ml of 10 percent acetic acid. The extracted copper in relation to the catalyst amount used is then determined.

The hydrogenation activity of the catalysts in the suspension hydrogenation of fatty acids was determined in the following way:

A 500 ml agitated autoclave is filled with 3 g of catalyst and 180 g of a commercial fatty alcohol mixture (CONDEA Alfol 1218). After activation of the catalyst at a temperature of 200° C. and a hydrogen pressure of 300 bar, the temperature is raised to 300° C.; then 20 g of lauric acid are added. During the course of the reaction, samples for the determination of the saponification value are taken from the reaction mixture. The degree of conversion can be defined at $$U = 1 - (VZ_t/VZ_o)$$

with t and o denoting the saponification values at a time t and at the outset of the reaction. Assuming first order kinetics the specific reaction velocity k and the half-life time $t_{\frac{1}{2}}$ can be expressed as $t_{\frac{1}{2}} = \ln 2/k$.

The following table summarizes the solubilities obtained for copper in the manner described above as a measure of the acid tolerance and the half-life times as a characteristic quantity for the hydrogenation activity. As a formal combination of these two criteria, a quality factor, equal to one thousand times the reciprocal of the product of the acid solubility and the half-value time was defined.

| Example | Acid solubility mg Cu/10 g catal. | Hydrogenation activity $t_{\frac{1}{2}}$ | Quality factor |
|---|---|---|---|
| A (comp) | 30 | approx 50 | 0.67 |
| B (comp) | 420 | 8.3 | 0.29 |
| C (comp) | 90 | 20.0 | 0.56 |
| 1 | 50 | 12.7 | 1.57 |
| 2 | 80 | 11.6 | 1.08 |
| 3 | 80 | 13.4 | 0.93 |
| 4 | 90 | 11.0 | 1.01 |
| 5 | 90 | 11.6 | 0.96 |
| 6 | 90 | 9.6 | 1.16 |
| 7 | 50 | 9.6 | 2.08 |

The examples clearly demonstrate the following effects:

If an SiO₂ component according to the invention is used, but the calcination is conducted at too high a temperature, the acid tolerance of the product is high, but the activity is extremely low (Comparative Example A).

If no SiO₂ component is added, after calcination in the temperature range according to the invention, a catalyst with high acid tolerance is obtained, but it has low activity (Comparative Example C).

If the calcination temperature is reduced, the activity is improved, but the acid tolerance decreases to an unacceptable value (Comparative Example B).

Only the combination of an SiO₂ component according to the invention with calcination in the temperature range according to the invention produces catalysts that combine high hydrogenation activity and high acid tolerance, which is formally documented in the higher quality factors.

The combination of an SiO₂ component according to the invention with an additional metal oxide promoter causes a synergistic effect; the best acid tolerance and the highest hydrogenation activity are obtained with simultaneous use of SiO₂ and ZrO₂.

The superiority of the catalysts according to the invention is further demonstrated especially when the catalyst is used repeatedly. The attached graphic illustration makes it clear that the deactivation of the catalyst according to the invention proceeds significantly more slowly. After 4 uses, the half value time is only about 85 percent that of the comparison catalyst, which causes a corresponding decrease in catalyst consumption.

What is claimed is:

1. An acid-resistant catalyst for the hydrogenation of fatty acids or fatty acid esters or mixtures thereof which consists essentially of (in analytical terms) about 20 to about 70 weights percent CuO, about 20 to about 70 weight percent Cr₂O₃, about 1 to about 25 weight percent SiO₂ having a porosity (determined by the nitrogen adsorption method) of <0.1 cm³/g, and 0 to about 15 weight percent of additional metal oxide selection from zirconium, cerium, or lanthanum oxide or mixture thereof, wherein said catalyst, after thermal treatment of the metal oxides or precursor compounds convertible into the oxides, has a specific surface area of about 8 m$^2$/g to about 60 m$^2$/g wherein the intensity ratio between the x-ray diffraction lines (XRD reflexes) of the copper oxide with d=0.232 nm and of the CuCr$_2$O$_4$ spinel with d=0.240 nm determined as a ratio of the reflex amplitudes is about 0.7 to about 40:1 and wherein the acid resistance as measured by the solubility of the copper in the catalyst in acid is a maximum of 200 mg as determined by stirring 10 grams of the catalyst in 10 weight percent acetic acid at 20° C. for 2 minutes.

2. The catalyst of claim 1 wherein the intensity ratio between the x-ray diffraction lines is 0.7 to 2.0:1.

3. The catalyst of claim 1 wherein the porosity is <0.05 cm$^3$/g.

4. The catalyst of claim 1 wherein the SiO$_2$ component is pyrogenic silicic acid, kieselguhr, or magnesium silicate.

5. The catalyst of claim 1 which contains (in analytical terms) about 30 to about 55 weight percent CuO, about 30 to about 55 weight percent Cr$_2$O$_3$, about 2 to about 15 weight percent SiO$_2$ and about 0.5 to about 10 weight percent zirconium, cerium, or lanthanum oxide or mixtures thereof.

6. The catalyst of claim 5 which contains (in analytical terms) CuO, Cr$_2$O$_3$, SiO$_2$ and ZrO$_2$.

7. The catalyst of claim 5 which contains (in analytical terms) CuO, Cr$_2$O$_3$, SiO$_2$ an Ce$_2$O$_3$.

8. The catalyst of claim 1 wherein the specific surface area is about 10 to about 40 m$^2$/g.

* * * * *

REEXAMINATION CERTIFICATE (3083rd)

United States Patent [19]
Schneider et al.

[11] B1 5,217,937
[45] Certificate Issued Dec. 24, 1996

[54] SIO$_2$-CONTAINING COPPER OXIDE-CHROMIUM OXIDE CATALYST FOR THE HYDROGENATION OF FATTY ACIDS AND FATTY ESTERS

[75] Inventors: Michael Schneider, Ottobrunn-Riemerling; Gerd Maletz, Brückmühl; Karl Kochloefl, Brückmühl/Heufeld, all of Germany

[73] Assignee: Sud-Chemie Aktiengesellschaft, Munich, Germany

Reexamination Request:
No. 90/003,937, Aug. 29, 1995

Reexamination Certificate for:
Patent No.: 5,217,937
Issued: Jun. 8, 1993
Appl. No.: 795,493
Filed: Nov. 21, 1991

[30] Foreign Application Priority Data

Nov. 27, 1990 [DE] Germany ................. 4037729

[51] Int. Cl.$^6$ ............. B01J 21/06; B01J 21/08; B01J 23/10; B01J 23/26; B01J 23/72
[52] U.S. Cl. ............. 502/242; 502/244; 502/524; 568/885
[58] Field of Search ............. 502/242, 244, 502/524; 568/885

[56] References Cited

FOREIGN PATENT DOCUMENTS

WO9104789  4/1991  WIPO.

*Primary Examiner*—Glenn Caldarola

[57] ABSTRACT

An SiO$_2$-containing copper oxide-chromium oxide catalyst is obtained through heat treatment of copper oxide and chromium oxide, or of a precursor compound convertible into copper oxide or chromium oxide in the presence of an SiO$_2$ component; it is characterized by the fact that, after the heat treatment, (a) the intensity ratio between the X-ray diffraction lines (XRD reflexes) of the copper oxide with d=0.232 nm and of the CuCr$_2$O$_4$ spinel with d=0.240 nm formed through heat treatment, determined as the ratio of the reflex amplitudes, is 0.7 to 4.0:1, and (b) the copper mass, which is dissolved by stirring 10 g of the catalyst in 100 ml of 10 weight percent acetic acid at 20° C. for 2 minutes, amounts to a maximum of 200 mg.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *